United States Patent [19]

Marinello

[11] 4,036,229
[45] July 19, 1977

[54] APPARATUS FOR ASSISTING THE TREATMENT OF WOUNDS OR INFLAMMATIONS INTERNAL TO THE HUMAN BODY

[76] Inventor: Rosolino Marinello, Viale Leonardo da Vinci No. 4, Mantova, Italy

[21] Appl. No.: 625,708

[22] Filed: Oct. 24, 1975

[30] Foreign Application Priority Data

Nov. 6, 1974   Italy ................................. 42690/74

[51] Int. Cl.² .............................................. A61F 7/02
[52] U.S. Cl. ................................... 128/268; 128/327
[58] Field of Search ................. 128/268, 327, 160; 119/1, 29, 143, 106

[56] References Cited

U.S. PATENT DOCUMENTS

| 37,156 | 12/1862 | Dunton | 128/327 |
|---|---|---|---|
| 1,199,052 | 9/1916 | Crawford | 128/327 X |
| 2,332,107 | 10/1943 | Nieburgs | 128/327 |
| 2,676,593 | 4/1954 | Cheneweth | 128/268 |
| 2,690,747 | 10/1954 | Frallic | 128/165 |
| 2,754,825 | 7/1956 | Richmond | 128/327 |
| 2,811,970 | 11/1957 | Hipps et al. | 128/327 |
| 3,050,064 | 8/1962 | Moore et al. | 128/327 |
| 3,213,830 | 10/1965 | Wiesemann | 119/106 |
| 3,333,586 | 8/1967 | Bellis et al. | 128/268 |
| 3,814,097 | 6/1974 | Ganderton et al. | 128/268 |

*Primary Examiner*—Aldrich F. Medbery
*Attorney, Agent, or Firm*—Brisebois & Kruger

[57] ABSTRACT

Apparatus for assisting the treatment of wounds or inflammations internal to the human body comprises a belt support consisting of a resilient base plate with belts connected to two of its opposite sides. The belts are arranged to encircle the human body, with a center hole in the plate lying on the area of the bodily disorder. A tube mounted on the plate above the center hole houses a sliding plug, on the underside of which is placed a suitable medicament. The plug passes through the hole and presses the medicament against the area of the disorder, the contact pressure being adjustable micrometrically by operating an upper handle rigid with a screw which engages in the plug.

4 Claims, 7 Drawing Figures

APPARATUS FOR ASSISTING THE TREATMENT OF WOUNDS OR INFLAMMATIONS INTERNAL TO THE HUMAN BODY

SUMMARY OF THE INVENTION

This invention relates to an apparatus applicable to adhere externally to the human body, for holding various medicaments against this latter.

It comprises substantailly a belt support which, in contrast to the usual belts normally used for containing hernias or the like, eliminates the undesirable constricting effect produced by the elastic belt in contact with a complete annular band of the bodu, and enables the adhesion of the medicament at the required pressure to be limited to the area representing the seat of the disorder.

The apparatus according to the invention consists substantially of a resilent base plate provided with belts on two opposing sides, and comprising a hollow cavity in which a plug axially slides, its base being designed to compress the area of the disorder by way of the interposed medicament, to an adjustable degree.

The apparatus will be more evident from the description given hereinafter with reference to the figures of the accompanying drawings, in which.

Figure 4:
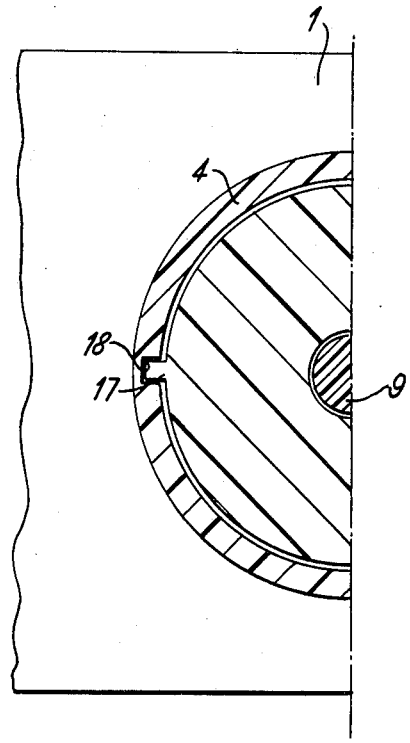
Figure 5:
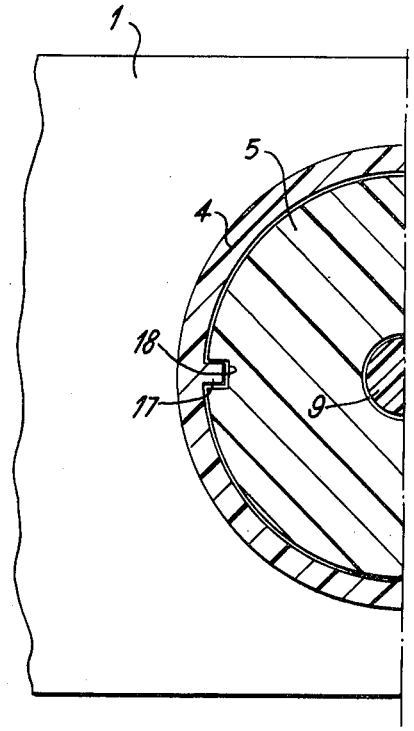
Figure 6:
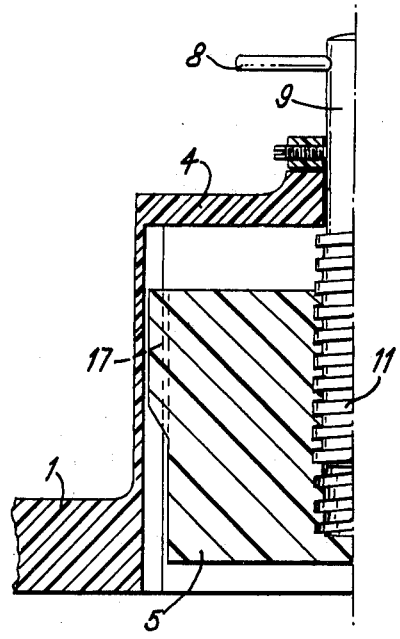
Figure 7:
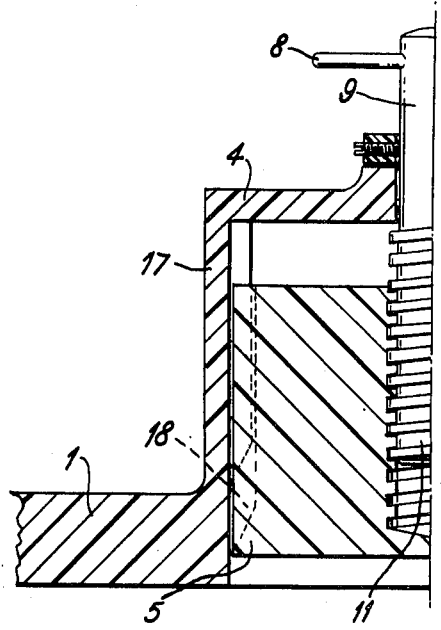

FIGS. 4 and 5 are horizontal sections through two different embodiments of the slidable engagement between the hollow body and plug; and FIGS. 6 and 7 are vertical sections corresponding to FIGS. 4 and 5 respectively.

Figure 1:
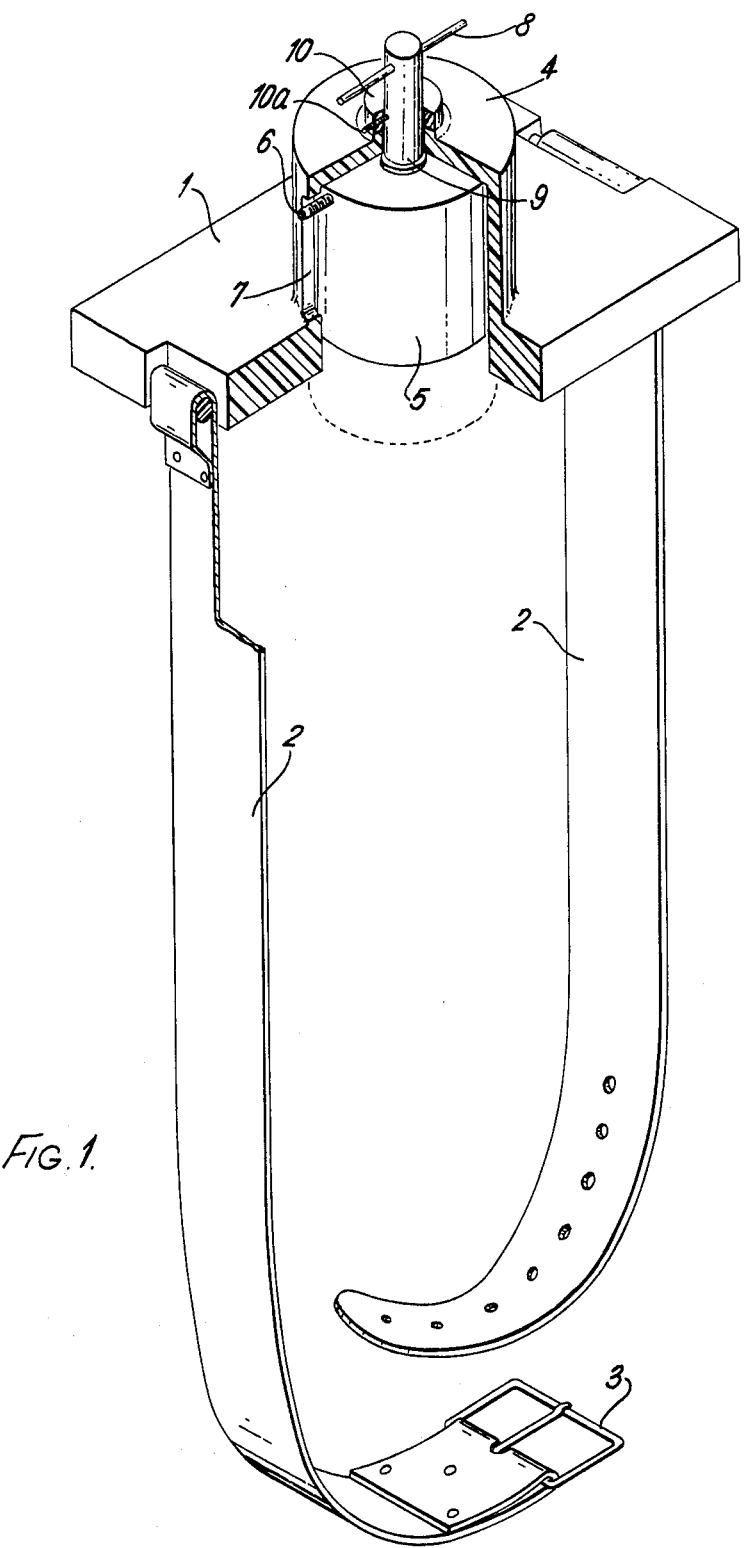
FIG. 1 is an isometric view of the apparatus in partial section.
Figure 2:
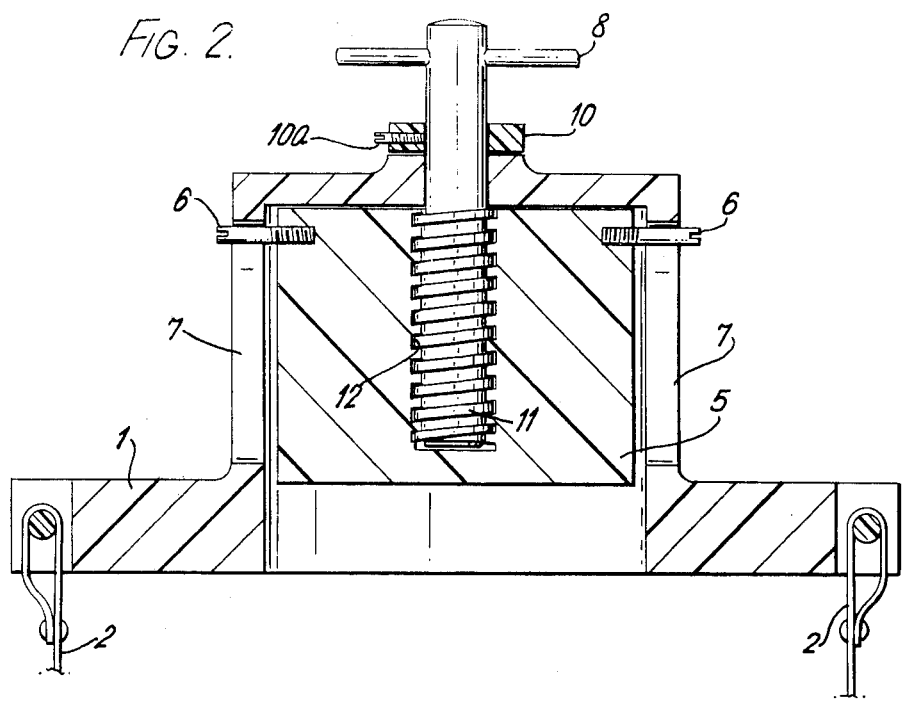
FIG. 2 is a vertical section through the apparatus.

FIGS. 1 and 2 show that the apparatus according to the invention consists of a base plate 1 formed from flexible material, especially at the edges, and comprising two belt portions 2 fixed to two opposing sides, and a buckle 3. At the centre of the plate 1 there is a through hole at which is fixed a hollow member 4 in which a preferably cylindrical plug 5 is mounted to slide telescopically along the two vertical guide slots 7 guiding the pegs 6. This sliding is adjusted micrometrically by operating the upper handwheel 8 rigid with the shaft 9, which comprises a formed screw portion 11 which screws into the threded bore 12 present at the centre of the aforementioned plug 5. The threaded shaft 9 is rotatably constrained to the hollow member 4 by the upper ring 10 and the upper shoulder of the threaded portion 11.

The ring 10 is locked on the shaft 9 by one or more screws 10a in ring 10.

This enables the shaft to rotate in the central hole of the hollow member 4 without making any vertical movement, thus causing the plug 5 to slide vertically.

The plug 5 has a suitable area on its underside or lower base surface for receiving medicament, and the vertical movement of the plug applies the medicament under continuing compression or pressure to the skin at the area of disorder.

Figure 3:
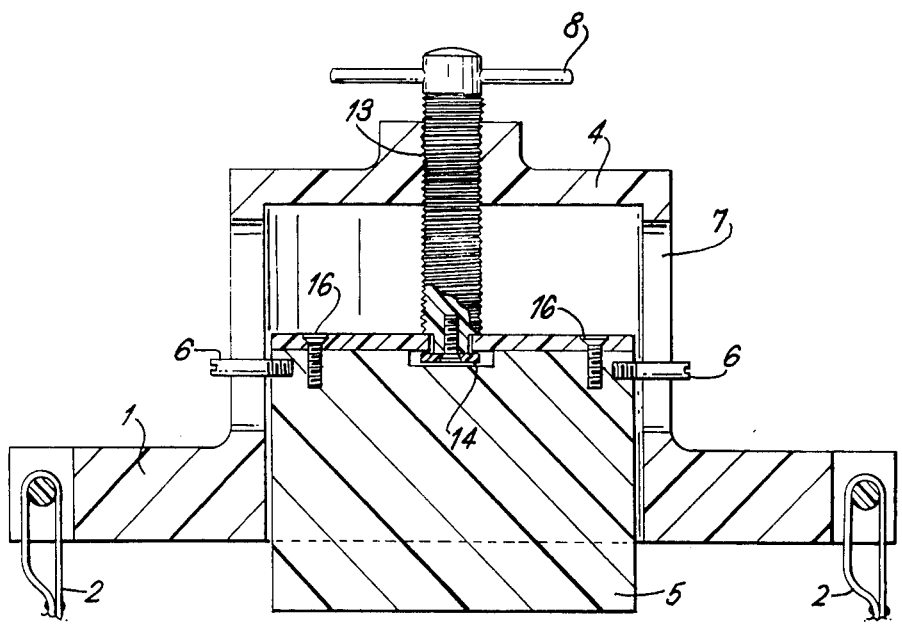
FIG. 3 is a vertical section through the apparatus according to the invention constructed in a different manner from that shown in FIG. 2.

According to a further embodiment, the vertical sliding of the plug 5 can be obtained by screwing the shaft 9 into the central hole 13 of the hollow member 4, as shown in FIG. 3, by providing it with a corresponding thread.

In this case the shaft 9 is rotatably engaged at its bottom with the plate 15 by way of the disc 14, the plate being fixed to the head of the plug 5 by screws 16.

Rotation of the plug is also avoided in this case by the pegs 6 engaging in the guides 7.

This latter characteristic can also be obtained differently, preferably in accordance with the two embodiments shown in FIGS. 4 to 7.

FIGS. 4 and 6 show one of these embodiments in which the plug 5 comprises two diametrically opposing vertical ribs 17 which engage in corresponding grooves 18 formed in the inside wall of the hollow member 4.

FIGS. 5 and 7 show the other embodiment, which is essentially the reverse construction of that shown in FIGS. 4 and 6 heretofore described. In this case the ribs 17 are formed on the inner wall of the hollow member 4, while the vertical grooves 18 are present on the periphery of the plug 5.

The plug pressure is adjusted after applying the medicament between the lower surface of the plug and the human body, and fastening the belt around this latter.

The invention is not limited to the single embodiment heretofore described, and modifications and improvements may be made to it without leaving the scope of the invention, the fundamental characteristics of which are summarised in the following claims.

What is claimed is:

1. Apparatus for treating limited areas of the skin, said apparatus comprising:
   a plate of resilient material defining a central hole extending through said plate,
   a means for applying continuing pressure to a medicament in contact with the skin at an area of disorder including
   a tube on one side of said plate having substantially the same inner diameter as said hole and coaxial therewith
   a plug slidably mounted in said hole and tube,
   screw means for moving said plug axially of said tube,
   cooperating guide means on said tube and plug for guiding said plug during said axial movement, and
   belt means connected to said plate for holding said plate against an area of the skin.

2. Apparatus as claimed in claim 1 comprising a medicament applied to said plug.

3. Apparatus as claimed in claim 2 in which said screw means comprises an end member at the end of said tube remote from said plate, said end member defining a threaded hole coaxial with said tube, and a screw having threads mating with those of said threaded hole and having one end rotatably attached to said plug while its other end passes through said threaded hole.

4. Apparatus as claimed in claim 2 in which said screw means comprises an end member at the end of said tube remote from said plate, said end member defining a hole coaxial with said tube, and a screw having a threadless portion mounted in the hole in said end member for rotational movement only, said plug having a threaded bore in which a threaded portion of said screw is received.

* * * * *